United States Patent

Munsch

[11] Patent Number: 5,840,151
[45] Date of Patent: Nov. 24, 1998

[54] APPARATUS AND DIES FOR FORMING PEELABLE TUBE ASSEMBLIES

[75] Inventor: John M. Munsch, Libertyville, Ill.

[73] Assignee: Baxter International Inc., Deerfield, Ill.

[21] Appl. No.: 747,776

[22] Filed: Nov. 13, 1996

Related U.S. Application Data

[63] Continuation-in-part of Ser. No. 694,799, Aug. 9, 1996, abandoned, which is a continuation of Ser. No. 299,534, Sep. 1, 1994, abandoned, which is a division of Ser. No. 299,800, Sep. 1, 1994, Pat. No. 5,466,322, which is a continuation of Ser. No. 13,447, Feb. 4, 1993, abandoned.

[51] Int. Cl.$^6$ ............................ B29C 65/00; B29C 65/04
[52] U.S. Cl. .................................... 156/380.2; 156/379.8; 156/380.6; 219/765; 219/769
[58] Field of Search ............................ 156/380.6, 379.8, 156/380.2; 219/769, 765

[56] References Cited

U.S. PATENT DOCUMENTS

| | | |
|---|---|---|
| 2,300,243 | 10/1942 | Zierden . |
| 2,433,546 | 12/1947 | Cornelius . |
| 2,457,498 | 12/1948 | Russell et al. . |
| 2,679,469 | 5/1954 | Bedford . |
| 2,816,596 | 12/1957 | Welch, Jr. . |
| 3,312,579 | 4/1967 | Heifetz . |
| 3,322,590 | 5/1967 | Clark . |
| 3,329,271 | 7/1967 | Ward et al. . |
| 3,537,935 | 11/1970 | Withers . |
| 3,558,397 | 1/1971 | Clark . |
| 3,580,764 | 5/1971 | Gerlach et al. . |
| 3,706,620 | 12/1972 | Dykstra . |
| 3,802,987 | 4/1974 | Noll . |
| 3,870,579 | 3/1975 | Uncapher . |
| 3,879,659 | 4/1975 | Lawson, Jr. . |
| 4,072,146 | 2/1978 | Howes . |
| 4,263,808 | 4/1981 | Bellotti et al. . |
| 4,276,333 | 6/1981 | Cobean . |
| 4,326,902 | 4/1982 | Peddie . |
| 4,389,267 | 6/1983 | Denslow . |
| 4,436,620 | 3/1984 | Bellotti et al. . |
| 4,486,253 | 12/1984 | Gonia . |
| 4,491,711 | 1/1985 | Acker ...................................... 219/769 |
| 4,555,293 | 11/1985 | French . |
| 4,576,671 | 3/1986 | Shimanaka . |
| 4,605,397 | 8/1986 | Ligon et al. . |
| 4,900,389 | 2/1990 | Schnell et al. . |
| 5,036,891 | 8/1991 | Vogelsang . |
| 5,049,224 | 9/1991 | Umezawa et al. . |
| 5,073,314 | 12/1991 | Coutandin . |
| 5,439,720 | 8/1995 | Choudhury . |

FOREIGN PATENT DOCUMENTS

| | | |
|---|---|---|
| 2054807 | 4/1971 | France . |
| 3614339 | 10/1987 | Germany . |
| 59-42920 | 3/1984 | Japan . |
| 59-42921 | 3/1984 | Japan . |
| 59-178214 | 10/1984 | Japan . |
| 60-4030 | 1/1985 | Japan . |
| 1497204 | 1/1978 | United Kingdom . |
| 9308978 | 5/1993 | WIPO . |
| 9417983 | 8/1994 | WIPO . |

*Primary Examiner*—Jeff H. Aftergut
*Attorney, Agent, or Firm*—Charles R. Mattenson; Thomas S. Borecki; Richard Beem

[57] ABSTRACT

An apparatus for forming coiled tubular assemblies is provided. The apparatus includes a pair of dies formed from a radio frequency (RF) conducting material. The dies each have contoured leading surfaces with these surfaces having grooves with lands between adjacent grooves. The lands of the dies cooperate to form web forming chambers when the pair of dies are moved together in their operative position. In the operative position, the tubes are captured in the aligned grooves with portions of the tubes being squeezed or extruded into the web forming chamber. Application of RF energy to the dies causes the tube portions in the chambers to plasticize and form webs between the coils of the tubes with a predetermined configuration substantially the same as that of the web forming chambers. Both radially coiled and axially coiled tube assemblies are contemplated by the invention. In addition, an easy-to-separate or peel tubular assembly is formed with the above apparatus.

7 Claims, 8 Drawing Sheets

APPARATUS AND DIES FOR FORMING PEELABLE TUBE ASSEMBLIES

CROSS-REFERENCE TO RELATED APPLICATION

This application is a continuation-in-part of U.S. patent application Ser. No. 08/694,799, filed on Aug. 9, 1996 and entitled "ELONGATE PLASTIC MEMBER ASSEMBLY AND METHOD FOR MAKING THE SAME", now abandoned, which is a continuation application of patent application Ser. No. 08/299,534, filed on Sep. 1, 1994, and entitled "ELONGATE PLASTIC MEMBER ASSEMBLY AND METHOD FOR MAKING THE SAME", which is a divisional application of U.S. patent application Ser. No. 08/299,800, filed on Sept. 1, 1994, now U.S. Pat. No. 5,466,322, issued on Nov. 14, 1995 which is a continuation of U.S. patent application Ser. No. 08/013,447, filed on Feb. 4, 1993, and entitled "ELONGATE PLASTIC MEMBER ASSEMBLY AND METHOD FOR MAKING THE SAME", now abandoned.

FIELD OF THE INVENTION

The invention relates to an apparatus for forming coiled tube assemblies which can be peeled to separate the tubular members of the assembly from one another, radio frequency dies of the assembly and an assembly of coiled tubular members which maintain a predetermined configuration by way of integral webs formed between adjacent coils of the tubular members.

BACKGROUND OF THE INVENTION

Utilizing tubular assemblies in parenteral or intravascular or intravenous (I.V.) solution delivery systems is known, such as for delivering fresh dialysate to patients having renal failure and being treated with peritoneal dialysis. These tubular assemblies typically have tubes which are connected to sources of parenteral or I.V. solution, such as in flexible bags or bottles, and deliver these solutions from their other end to the patient. It is often desirable that several tubes be provided in an assembly such that greater volumes or multiple batches of the same liquid and/or different solutions can be provided to the patient, as well as draining liquids, such as parenteral solution, from the patient. Oftentimes, these medical devices using tubular assemblies are provided for home use so as not to require the patient to travel to a hospital or other medical facility to obtain treatments. In this context, it is particularly important that the patient be able to properly fit up the tubes to solution supplies and drains and to themselves. This is particularly becoming more common with treatments for kidney-related disorders which affect the filtration function of the kidneys, such as with home-use peritoneal dialysis equipment. Typically, the tubular assemblies will be provided in a coiled configuration by bunching the individual tubular members together and bending and winding them into a coiled configuration and either taping or placing a band of some sort around the tubes. It would be preferable that the patients be able to avoid any potential set-up difficulties such as may occur if they are required to remove the tape or band placed around the tubes and then unravel the tubes from each other before using the tubes for their delivery and/or drainage functions.

In this regard, it is known in the art to integrally connect adjacent tubes to each other. In this manner, the tubular assembly is maintained in a predetermined configuration so that the tubes are relatively tangle-free when provided to the patient. However, tubes that are connected in parallel along their entire length, such as by integral extrusion methods, present several problems. One problem is that the tubular members are not in their most compact form as would be desirable for assembly and packaging. Compactness is economically desirable and also saves sterilization time because a compact tube assembly reduces air volume in the overpouch. Another problem is that by connecting the tubes to each other along their entire length, the patient, such as a peritoneal dialysis patient, must spend a great deal of time and effort separating the tubes from each other for use. As many peritoneal dialysis patients are in a weak or infirm state, the lengthwise connection between the tubes and the accompanying work required for separation is undesirable.

As such, providing the connections between the tubes at intervals as opposed to a continuous connection along the length of the tube is preferred over the above-described continuous connections. However, it is still desirable to maintain the tubular assemblies in a compact form and tube assemblies initially formed in a straight line or parallel tube-to-tube orientation have webs with a corresponding straight configuration that can be torn or broken by bending or coiling to get them in a more compact form. Thus, pre-forming the tubular assemblies in a coiled configuration is desirable. An example of such a coiled tubular assembly and an apparatus for making these assemblies is disclosed in U.S. Pat. No. 4,276,333 to Cobean, commonly assigned to the assignee herein. Cobean discloses a fairly complex apparatus for dispensing solvent across coils of a single tube wound on a cylindrical mandrel. To attempt to ensure that the solvent dispensing apparatus provides an appropriate amount of solvent along the coiled tubular member, an arrangement of stationary and moving pivot mounts for a syringe and a rigid arm of the apparatus is provided so that the rate at which solvent is dispensed across the coiled tube is a function of the rate at which the syringe is moved transversely across the coils. In other words, the slower the syringe is moved, the lower the dispensing rate for the solvent; conversely, increasing the rate of syringe travel will correspondingly increase the rate of solvent dispensed. The apparatus of Cobean dispenses solvent from the syringe onto the coils with capillary action spreading the solvent between adjacent coils to form a weak bond along portions of the adjacent coils to which the solvent is spread. Once the bond is formed, the axially coiled assembly is removed from the mandrel in its helical or axially coiled configuration.

The use of solvent bonding to form these tubular assemblies is undesirable in several respects. Solvents tend to generate potentially noxious fumes as the solvent volatilizes into the surrounding air when drying. This requires that a sufficient ventilation system be provided complying with applicable governmental regulations and ordinances relating to workplace safety. Also, special structure must be provided for the dispensing syringes to eliminate any trapped air therein, such as the double check valve taught by Cobean, which could hinder the accurateness of their dispensing function as in the apparatus of Cobean. As evidenced by the efforts of Cobean, the application of solvent has to be closely controlled so as to only apply the amount of solvent necessary to form the desired connection between the tubes. This is particularly important where thinner walled tubes are present as imprecise web formation, such as by delivery of too much solvent, can compromise the tube wall integrity to the extent that it is not usable or safe for use, particularly after breaking of the webs to separate the coils.

Despite improvements in Cobean with respect to solvent dispensing, the ability to control the formation of the connection or webs between the adjacent tubes is still limited as Cobean relies on capillary action for spreading of the solvent. Thus, it is desirable to be able to more accurately control the formation and final configuration of the integral webs and in this manner exercise more precise control over the pull force required to "peel" or separate adjacent coils from each other.

Other methods for welding plastic include ultrasonic welding which can present similar problems with respect to control over the integral web formation as with the solvent bonding method of Cobean as ultrasonic welding relies on rapid agitation of joint areas to create frictional heat for melting the plastic of the tubes. The ultrasonic horn, in contact with the plastic component to be welded, transmits the ultrasonic vibrations to the plastic/metal interface. Surface-to-surface frictional forces generated by ultrasonic energy primarily only create heat at the surface location of the frictional forces and thus the use of ultrasonic energy is not a particularly effective method for controlling the bonds formed thereby. With the agitation of the joint areas, significant attention to the fixturing utilized is also required to ensure adequate and proper alignment, clamping and support. Also, when attempting to use ultrasonic bonding or welding with plastics incorporating fillers for improved rigidity and weldability, wear of the horn may be accelerated. The use of mold release agents can also defeat the frictional heat developed at the interface. Horn wear and inconsistent heat formation contribute to the lack of precise control over the frictional melting and bonds formed thereby.

Thus, there is a need for an apparatus for forming tubular assemblies of multiple tubes which can be peeled from each other where the control over the formation and configuration of connecting webs formed between adjacent coils is very precise. Similarly, there is a need for an assembly of tubes with integral webs between adjacent coils which allows the tubes to be easily separated from each other such as by a single pull on one end of the tubes.

SUMMARY OF THE INVENTION

In accordance with the present invention, an apparatus for forming coiled tube assemblies which can be peeled to separate the tubular members from one another, a set of radio frequency dies utilized to connect spaced portions of adjacent tubular members together and an assembly of tubular members maintained in a predetermined coiled configuration are provided which overcome the above problems of the prior art.

One aspect of the invention is a set of radio frequency dies utilized in an apparatus for forming peelable plastic tubular assemblies. The dies are placed about the tubular members to connect spaced portions of adjacent tubular members together.

In one form, the apparatus includes a pair of dies having respective leading surfaces which are spaced at a first predetermined distance from each other in a tube-receiving first position and in a second operative position, they are spaced at a second predetermined distance less than the first distance for forming the tube assembly. The dies are formed from an RF energy conducting material. A plurality of cooperating grooves are formed in the leading surfaces of the dies with the grooves of the dies aligned with each other to cooperate to define die bores in the operative position. The die bores are sized to engage and radially compress the tubular members without occluding the flow passages of the tubes. A land is provided between pairs of adjacent grooves of the leading surfaces of the dies with corresponding facing lands on the die surfaces defining flow chambers for portions of the tubular members near the flow chambers. These tubular member portions are plasticized upon application of RF energy to the dies and form connecting webs of plastic between adjacent tubular members in the flow chambers when the dies are in their operative positions. By utilizing dies formed from an RF energy conducting material and having lands which form flow chambers for portions of the tubular members near the chambers, the connecting webs of plastic formed between adjacent tubular members can be closely controlled by controlling the size of the flow chambers. As the apparatus utilizing the radio frequency dies directs a large amount of RF energy into the work area, i.e., between the lands in the flow chambers, to cause the extruded portions of the tubes in the chamber to melt and intimately intermingle, a more uniform and consistently formed connecting web can be obtained.

Preferably, the die bores are smaller than the diameter of the tubular members. In another form, the grooves defining the die bores have a flat bottom surface, spaced from adjacent lands at a distance to squeeze the tubular members to extrude the outer tubing walls between opposing lands with the dies in the operative position. With the dies in their operative position, the flat bottom surfaces of aligned cooperating grooves in the dies can be spaced at a compression distance that is less than the outer diameter of the tubular members to radially compress the tubular members. The compression distance between the grooved bottom surfaces can be approximately 80% of the tubular member's outer diameters. In this manner, when the dies are moved to their operative position, the tubular members will be squeezed so that the portions near the flow chambers will extrude into the flow chambers to be melted by RF energy as it is applied to the dies of the apparatus.

In a preferred form, the tubular members are coiled about an axis with the dies in the tube-receiving position and two pairs of die sets are provided to form the plastic connecting webs at opposite portions of the coils of the tubular members such that a coiled tube assembly is formed with the individual tubular members peeled from the assembly and separated from each other with breaking of the webs without damaging the walls of the tubular members. In this fashion, a compact coiled tube assembly is provided with the tubes easily separated from one another by breaking the webs.

In another form, the tubular members are coiled radially about an axis with the outer tubular member of the coiled tubular members having the largest radius from the axis and the inner tubular member coil having the smallest radius from the axis. The grooves include arcuate portions, each having a radius substantially equal to the radius of the corresponding coil of the coiled tubular members, with the radius of the arcuate portions progressively decreasing from the outer groove to the inner groove. The arcuate portions of each groove can include an outer arcuate side and an inner arcuate side each having a radius with the radius of the inner side and the radius of the outer side of the grooves each being different from the radius of the respective inner and outer sides of another adjacent groove by the diameter of the tubular members and the width of the land between the grooves. The lands can have an arcuate shape having a radius with the radius of the arcuate lands progressively decreasing from the outer land to the inner land for forming arcuate-shaped connecting webs between the coiled tubular members. In this manner, an efficient coiled tube assembly is provided without requiring subsequent bending or coiling which could place undue stress on the webs.

Another aspect of the invention is an apparatus for forming coiled tube assemblies of plastic tubular members.

The apparatus includes a die set including aligned die members having aligned grooves and lands between the grooves. In their operative position, the aligned grooves of the die set cooperate to define arcuate tube-receiving bores or channels and the aligned lands cooperate to define web forming chambers therebetween. A mounting device is provided for at least one of the die members to move the die members to the operative position. An RF energy generator applies RF energy to the die members to develop an energy potential between aligned lands sufficient to plasticize portions of the tubular members proximate the web forming chambers with the plasticized plastic flowing into the chambers to form a web between adjacent tubular members.

In one form, the tubular members are coiled radially about the axis. The grooves have an arcuate shape with aligned grooves cooperating to define arcuate tube-receiving channels. The lands have an arcuate shape with aligned lands cooperating to define arcuate web-forming chambers for forming arcuately shaped connecting webs between adjacent tubular members. The radially coiled tubular assembly is a very compact form of arranging the tubular members as they are maintained in a substantially flat configuration relative to each other.

In another form, the tubular members are coiled radially about the axis and the mounting device includes a pair of mounting plates with the coiling axis oriented perpendicularly to the plates. A pair of die sets is provided with one of the die members from each of the die sets mounted to one of the plates and the other die member from each of the die sets mounted to the other plate for movement to their operative position.

In another form, the mounting device includes a cylindrical mandrel having a cylindrical axis substantially coinciding with the coiling axis, with the tubular members coiled axially about the mandrel. In this form, the apparatus creates axially coiled tube assemblies.

Another aspect of the invention is an assembly of tubular members which are maintained in a predetermined coiled configuration. The coiled tube assembly includes first and second elongate tubular members with one of the tubular members coiled within the other tubular member. A crossover portion of the one tubular member at a side of the coil is provided which extends over the other tubular member for coiling of the one tubular member within the other tubular member. A plurality of integral webs are formed between adjacent coils of the tubular members to maintain the coiled assembly in its predetermined coiled configuration and allow a single pull force to break the webs to separate the tubular members from each other. The provision of a coiled tube assembly which can be peeled by way of a single pull force is a significant improvement over coiled tubes where each coil of the tubes are next to a coil of another tube which would require a second separation step. This is of special significance to those patients whose condition does not allow them to exert substantial energy in peeling tube assemblies.

Preferably, the webs have an arcuate shape and a predetermined thickness between adjacent coils. By precisely controlling the configuration of the webs, the pull force required to break the webs can likewise be regulated and adapted to the requirements of the medical application with which the tube assembly is to be used.

In one form, the crossover portion extends over an inner coil of the other tubular member.

Preferably, the tubular members are coiled radially about an axis with the outer coil of the one tubular member attached to the inner coil of the other tubular member through the integral webs. The integral webs can include one set of webs formed at a predetermined position along the coils and another set of webs formed at a second predetermined position along the coils on opposite sides of the axis relative to the first predetermined position. The coils can have a generally circular or oblong configuration and the web sets can be spaced 180° from each other along the coils.

DETAILED DESCRIPTION OF THE PREFERRED EMBODIMENT

Figure 1:
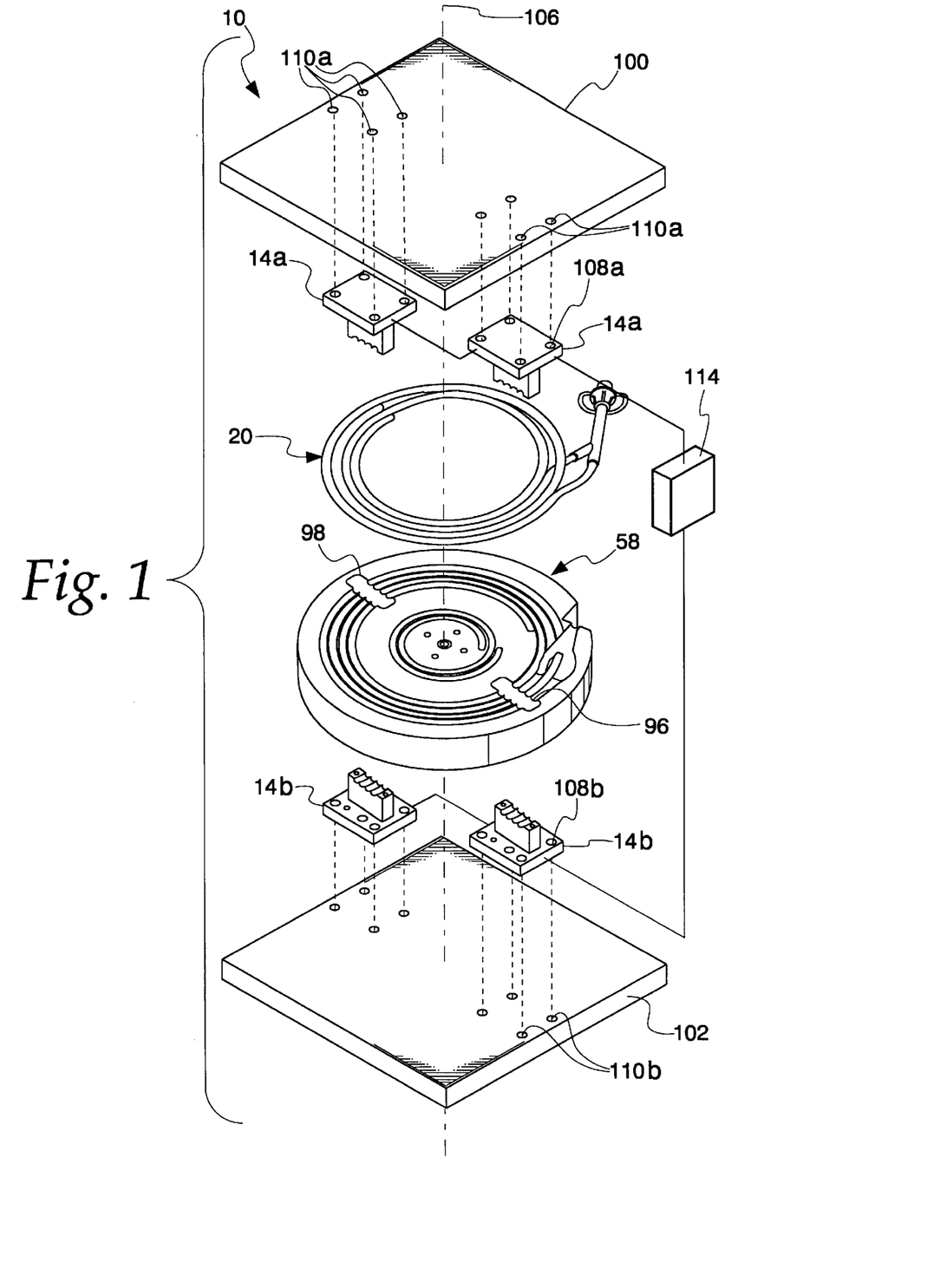
FIG. 1 is an exploded perspective view of the apparatus for forming peelable tube assemblies of plastic tubular members according to the invention showing radio frequency die sets and a platen for coiling the tubular members.

In FIG. 1, an apparatus 10 for forming peelable tube assemblies 12 of tubular members, such as tubular members 12a and 12b is illustrated. The apparatus 10 utilizes die assemblies 14 having a die 16 with a body 18 formed of an RF energy conducting material, such as brass. In this manner, an RF generator (not shown) can apply high frequency energy to the die bodies 18 generating an energy potential between a pair of dies 16 in close proximity to each other. When portions of the coiled plastic tubular members 20 are placed in the work area between the dies 16 and are subject to a large amount of RF energy created therein, as will be more fully described herein, the plastic in the work area will melt or plasticize as the RF energy causes the molecules of the material to oscillate, creating heat. Preferably, the tubular members 12a and 12b are formed from plastic material with a high dissipation factor, such as PVC. The high dissipation factor of the PVC plastic enables it to rise in temperature in the radio frequency field developed in the work area. When the heat exceeds the melting point of the PVC material, the material will collapse or melt. The melted portions will intimately intermingle to form a uniform and consistent joint or connection between adjacent coils of the tubular members 12a and 12b to connect the coils and form the peelable tube assembly 12. By closely controlling the configuration of the dies 16 and the distance between the dies 16 in forming the work area, the configuration and, thus, the strength of the connecting webs 22 can likewise be controlled so as to precisely determine the pull force required to break the webs 22.

More specifically and referring to FIGS. 6–9, the die bodies 18 have curved ends 24a and 24b, opposite sides 26a and 26b and a leading surface 28 which extends at the top of and between the curved ends 24 and the sides 26. The leading surface 28 of the die body 24 is machined with grooves 30 extending transversely across the leading surface 28 between the sides 26. Between adjacent grooves 30, a raised land 32 is formed which likewise extends transversely across the leading surface 28 between the sides 26 of the die body 18. The geometry of the grooves 30 and lands 32 therebetween are particularly important so that when aligned dies 16 are brought together to their operative position, the tubular members 12a and 12b of the peelable tube assembly 12 are captured in die bores or channels 34 formed by aligned grooves 30. The die bores 34 are sized so that they radially compress the tubes without occluding the flow passages 36 in the tubes with the compressed tubes having portions of their walls near the juncture of the grooves 30 and lands 32 squeezed or extruded into a web-forming chamber 38 defined between two confronting or facing lands 32. The spacing of the confronting lands 32 is such that when the generator fires to apply RF energy to the dies 16, an RF energy potential will develop in the work area or web-forming chambers 38 heating the tube wall portions extruded in the chambers 38, as previously described, to form the connecting webs 22 therein. On the other hand, the spacing of the surfaces of the grooves 30 is such that no plasticizing or melting of the tube walls occurs except for those tube wall portions extruded into the web-forming chamber 38, as described above.

Figures 2, 3, 4:
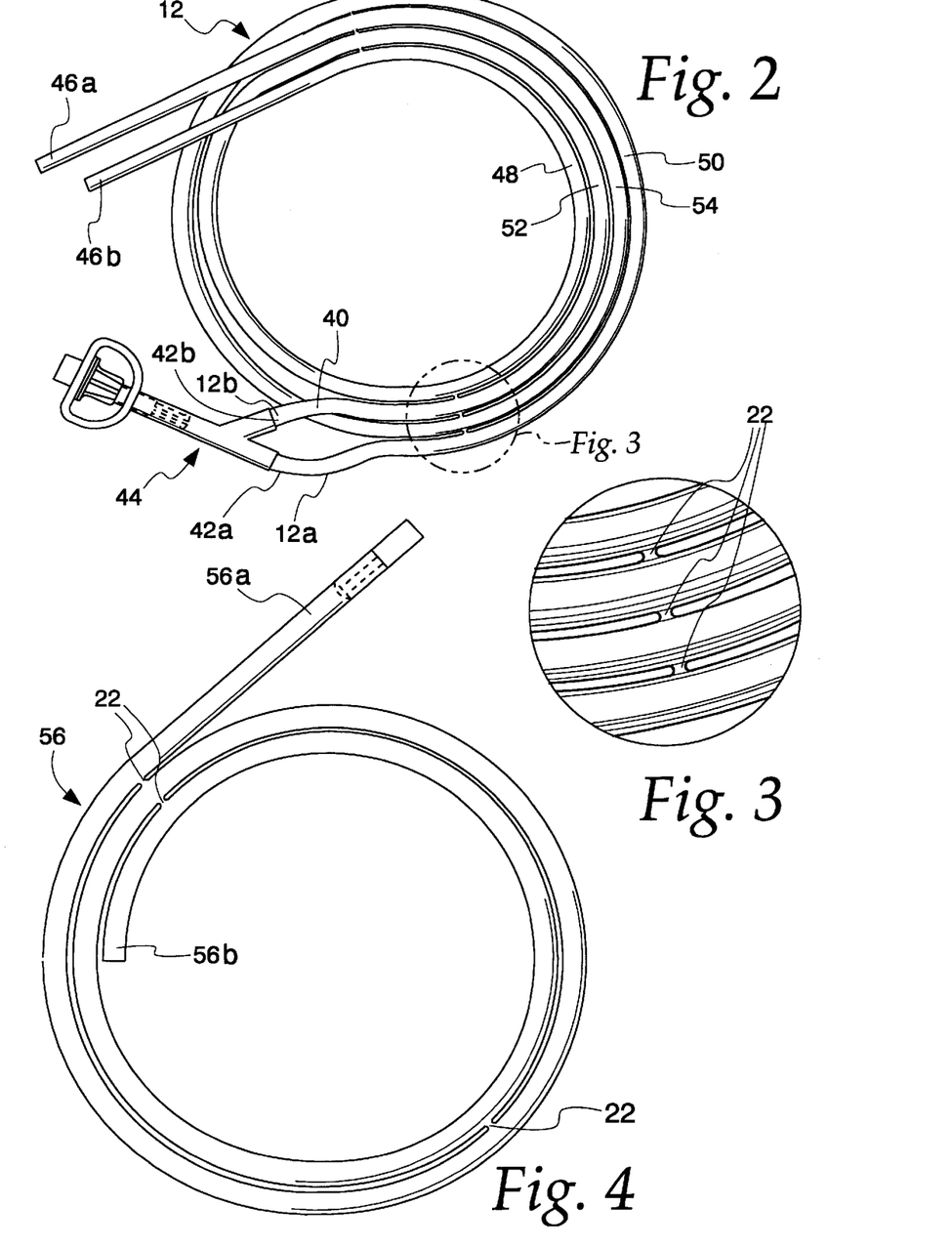
FIG. 2 is a plan view of two elongate tubular members maintained in a predetermined coiled configuration by way of a plurality of integral webs formed between adjacent coils of the tubular members.
FIG. 3 is an enlarged portion of the coiled tube assembly to show the slight curvature of the integral webs between adjacent coils.
FIG. 4 is a plan view of a single tube in a coiled configuration with integral webs for maintaining the tube in its coiled configuration.

Referring to FIGS. 2 and 3, it is preferred that the coiled peelable tube assembly 12 such as formed with the apparatus 10 be easily separated into individual tubular members 12a and 12b by the patients, particularly those in a weakened state. Thus, the preferred peelable tube assembly 12 herein allows a patient to exert a pull force on one end of the tubes 12a and 12b and break the connecting webs 22 between the adjacent coils of the tubular members 12a and 12b. More specifically, the first elongate tubular member 12a can be the outer tube and the second elongate tubular member 12b can be the inner tube by way of the provision of a crossover portion 40 on the inner tubular member 12b, as best seen in FIG. 2. The tubular members 12a and 12b have respective ends 42a and 42b which can be placed in a Y-shaped fitting 44. The other ends 46a and 46b of the respective tubular members 12a and 12b can be the free ends of the tubes. With the tube ends 42a and 42b securely connected in the fitting 44, the patient can grab the fitting 44 in one hand and the free ends 46 of the tubes 12 in their other hand and by exerting a pull force, such as on the fitting 44 or on the free ends 46 or on both, break all the webs 22 between the adjacent coils of the tubes 12a and 12b in a single separating step and thereby peel the tubes 12a and 12b from one another in a relatively quick and easy fashion.

The more efficient peeling of tubes 12a and 12b from their coiled connected form in the tube assembly 12 would not be possible if the tubes were wound in a coil with each of their coils adjacent a coil of the next tube. Coiling the tubes in this fashion would require a second separation step in that after a first pull which would uncoil the tubes, the two tubes would still be attached along their length by intermittent webs which would have to be broken by pulling on each individual tube end in a second step to separate the individual tubes from one another. By contrast, the interweaving of the tubular members 12a and 12b via the crossover portion 40 produces a coiled configuration wherein the innermost coil 48 of the inner tubular member 12b and the outermost coil 50 of the outer tubular member 12a are not adjacent a coil of the other tube. Instead, only the outer coil 52 of the inner tubular member 12b and the inner coil 54 of the outer tubular member 12a are attached by integral webs 22. Thus, exerting a pull force on the tubular members 12a and 12b in the peelable tube assembly 12 will break both the webs 22 between coils of the same tube such as coils 48 and 52 of the inner tube 12b and coils 50 and 54 of the outer tube 12a for uncoiling the tubular members 12a and 12b, and the same pull force will also break the webs 22 between the adjacent coils of the different tubes such as outer coil 52 of the inner tube member 12b and inner coil 54 of the outer tube 12a to separate the individual tubes 12a and 12b from each other. Of course, the dies 16 herein can also be used to produce connecting webs 22 for assemblies of more than two tubes and also for a single coiled tube 56, such as shown in FIG. 4. The single coiled tube 56 can also be uncoiled into a straight form by holding and pulling on respective ends 56a and/or 56b of the tube 56 as with the tube assembly 12.

Figure 5A:
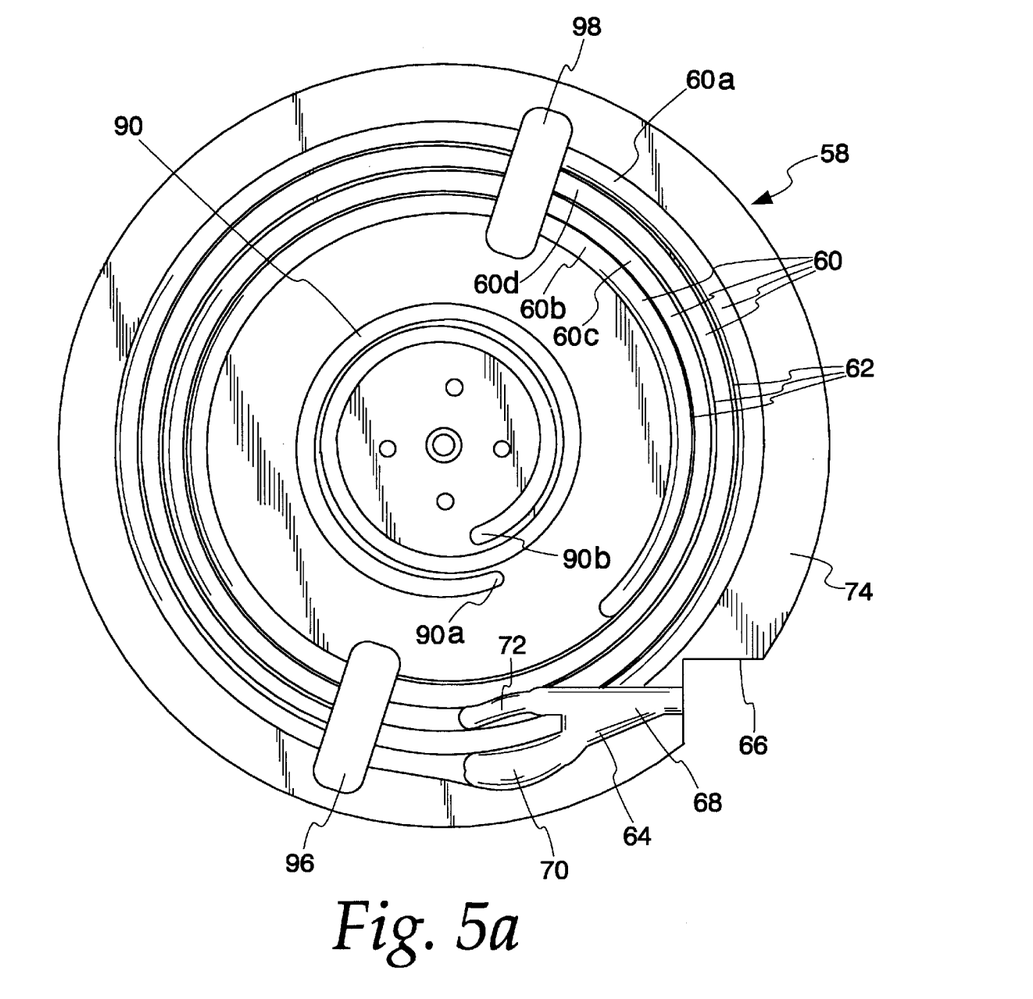
FIG. 5A is a plan view of the platen showing the circular grooves for the tubular members and the slots formed in the platen for receiving the dies.

To place the tubes 12a and 12b in their coiled configuration and in position and proper alignment with the dies 16 to be assembled into the peelable tube assembly 12, the apparatus 10 includes a grooved circular platen 58. The platen 58 is best shown in FIG. 5A and includes a plurality of generally circular grooves 60 formed therein. The grooves 60 of the platen are configured so that they become progressively smaller from the outer groove 60a to the inner groove 60b. The radius of the outermost groove 60a corresponds to the desired radius of the outermost coil 50 of the tube assembly 12. The decrease in radius of adjacent grooves from one to the next corresponds to the length of the diameter of the tubes 12 plus the width of lands 62 formed between adjacent grooves 60. The width of the platen grooves 60 and lands 62 corresponds to the width of the die grooves 30 and lands 32. As the lands 62 are relatively narrow, preferably on the order of 0.020 inches, the lands 62 need to be formed from a relatively strong material. It has been found that forming the platen 58 from an aluminum material will satisfy the strength requirements for the narrow lands 62.

For aligning the tubular members 12a and 12b into their coiled configuration described earlier, the platen 58 is provided with a lead-in portion 64. The platen 58 has a notch 66 cut in its periphery with the lead-in portion 64 extending from the notch 66 to the grooves 60 and being configured so as to fit the Y-shaped fitting 44. Thus, the lead-in portion 64 is provided with a main recessed portion 68 leading to a pair of recessed fingers 70 and 72 which, in turn, lead to grooves 60 of the platen 58. The grooves 60 are generally semi-cylindrical in cross-sectional shape with a radius substantially the same or slightly smaller than the radius of the tubular members 12a and 12b. In this manner, after the tubular members 12a and 12b are wound in their coiled configuration on the platen 58 in the grooves 60, the tubular members 12a and 12b will be substantially flush with the top surface 74 of the platen 58 or protrude only slightly thereabove. The lead-in portion 64, including the main portion 68 and recessed fingers 70 and 72 thereof, are recessed to a greater depth than the depth of the grooves 60. The recessed finger 70 leads to the outermost groove 60a in which the outermost coil 50 of tubular member 12a will seat. The recessed finger 72 leads to intermediate groove 60c in which the outer coil 52 of the tubular member 12b will seat.

Figure 5B:
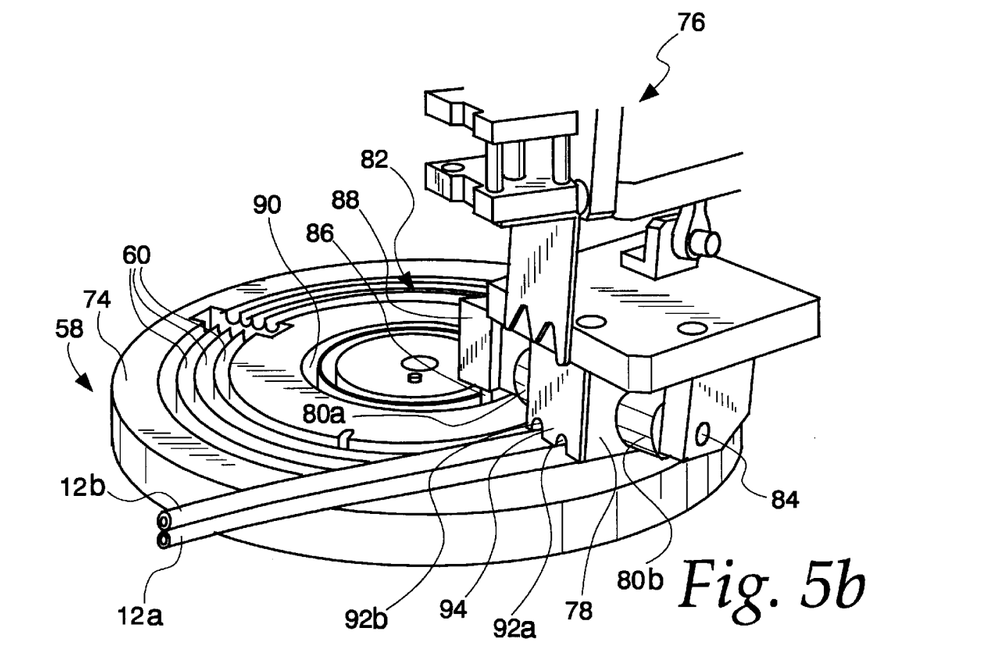
FIG. 5B is a perspective view showing a coiling apparatus for coiling the tubes in the grooves of the platen.
Figure 5C:
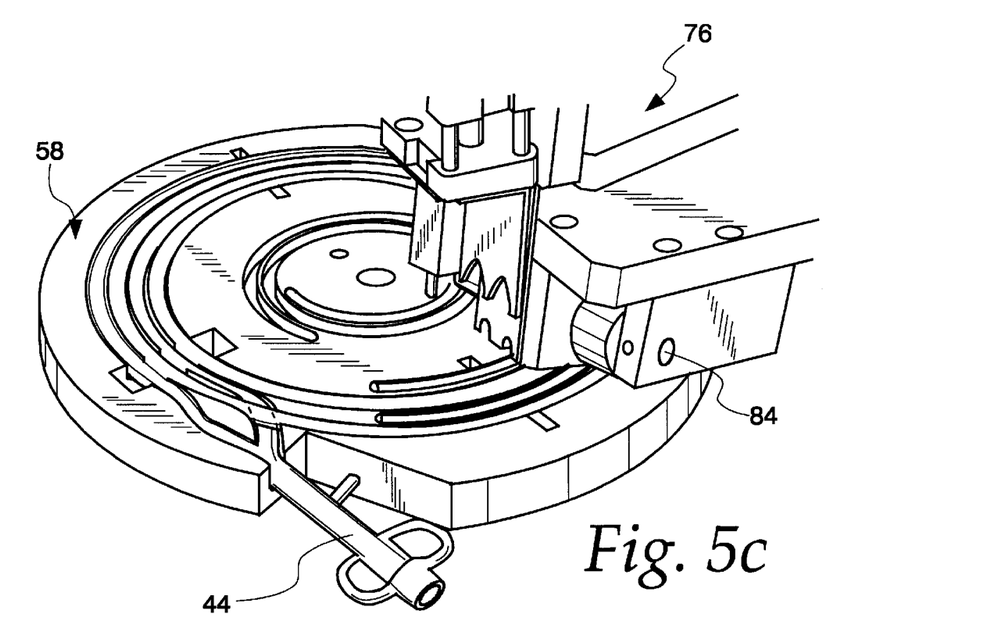
FIG. 5C is a perspective view showing the tubes coiled in the platen grooves with the coiling apparatus in its inoperative position.

To wind the tubes 12a and 12b in the grooves 60 of the platen 58, a tube winding or coiling apparatus 76 is provided as shown in FIGS. 5B and 5C. The coiling apparatus 76 includes a guide head 78 and a pair of rollers 80 on either side of the head 78 with the rollers 80 and head 78 mounted on axle 84. Thus, the rollers 80 include an inner roller 80a and an outer roller 80b. A tracking portion 82 is connected to the axle 84 of the rollers 80 and guide head 78 radially inwardly from the inner roller 80a. The entire coiling apparatus 76 can be pivoted from an inoperative position where the rollers 80 are disengaged from the top surface 74 of the platen 58, as seen in FIG. 5C, to an operative coiling position where the rollers 80 are in rolling contact with the top surface 74 and a pin follower 86 depending from block body 88 of the tracking portion 82 extends into a spiral cam groove 90 formed centrally and radially inwardly of grooves 60 on the platen 58.

Before starting the winding process, the Y-shaped fitting 44 with tube ends 42a and 42b secured therein is placed in lead-in portion 64, as seen in FIG. 5C, with the coiling apparatus 76 and particularly the guide head 78 thereof in front of the fitting 44 and the tubes 12a and 12b extending in a substantially straight orientation, as seen in FIG. 5B. Then, the coiling apparatus 76 is pivoted down to its operative position with the pin follower 86 in the radially outermost portion 90a of the spiral cam groove 90, as illustrated in FIG. 5B. The guide head 78 has a pair of spaced guiding and aligning grooves 92a and 92b which serve to maintain the tube members 12a and 12b seated in their appropriate grooves 60 as the coiling apparatus 76 is turned. Turning the coiling apparatus 76 in a counter clockwise direction from the position of FIG. 5B causes the guide head 78 to move radially inward as the pin follower 76 is caused to progressively move radially inward itself as it tracks in the spiral cam groove 90 from the radially outermost portion 90a to the radially innermost portion 90b until the tubes 12a and 12b are completely coiled in the grooves 60 of the platen 58, as seen in FIG. 5C.

It should be noted that the configuration of the spiral cam groove 90 is carefully coordinated with the required movement of the guide head 78 to properly coil the tubes 12a and 12b in the platen grooves 60. As mentioned above, initially the tubes 12a and 12b freely extend from the fitting 44 in a generally straight configuration through the aligning grooves 92a and 92b forwardly of the head 78, as seen in FIG. 5B. The alignment grooves 92 of the guide head 78 are spaced from each other by a central portion 94 with the width of the central portion 94 substantially corresponding to the width across one of the platen grooves 60 and lands 62 on either side thereof. In this manner, the tube members 12a and 12b are coiled with their respective outer coils 50 and 52 first being positioned in the corresponding platen grooves 60a and 60c spaced apart by platen groove 60d with the central portion 94 tracking over the groove 60d as the platen 58 begins its rotation. Continued rotation of the platen 50 and progressive inward radial movement of the guide head 78 causes the tubes 12a and 12d to coil within their respective outer coils 50 and 52. As previously mentioned, the lead-in portion 64 is recessed below the grooves 60 such that the crossover portion 40 formed near the tube end 42b of the inner tube 12b will seat in the recessed finger 72 and not interfere with continued coiling of the outer tube 12a. Thus, as the outer tube 12a is coiled so that its inner coil 54 seats in the intermediate platen groove 60d, a portion of the tube 12a will extend over the crossover portion 40 in the groove 60d. After the tubes 12a and 12b are attached by webs 22 and formed into the peelable tube assembly 12, the crossover portion 40 will extend over a side of the coil 54 of the tube 12a so that the tube 12b is coiled within the coiled tube 12a, as previously described.

Once the tubes 12 are coiled appropriately in the platen grooves 60 by operation of the coiling apparatus 76, the previously described connecting webs 22 can be formed between adjacent coils along spaced portions of the tube walls. In particular, the platen 58 is provided with a pair of die-receiving slots 96 and 98 spaced 180° from each other around the circular grooves 60 of the platen 58, as best seen in FIG. 5A.

Figure 6A:
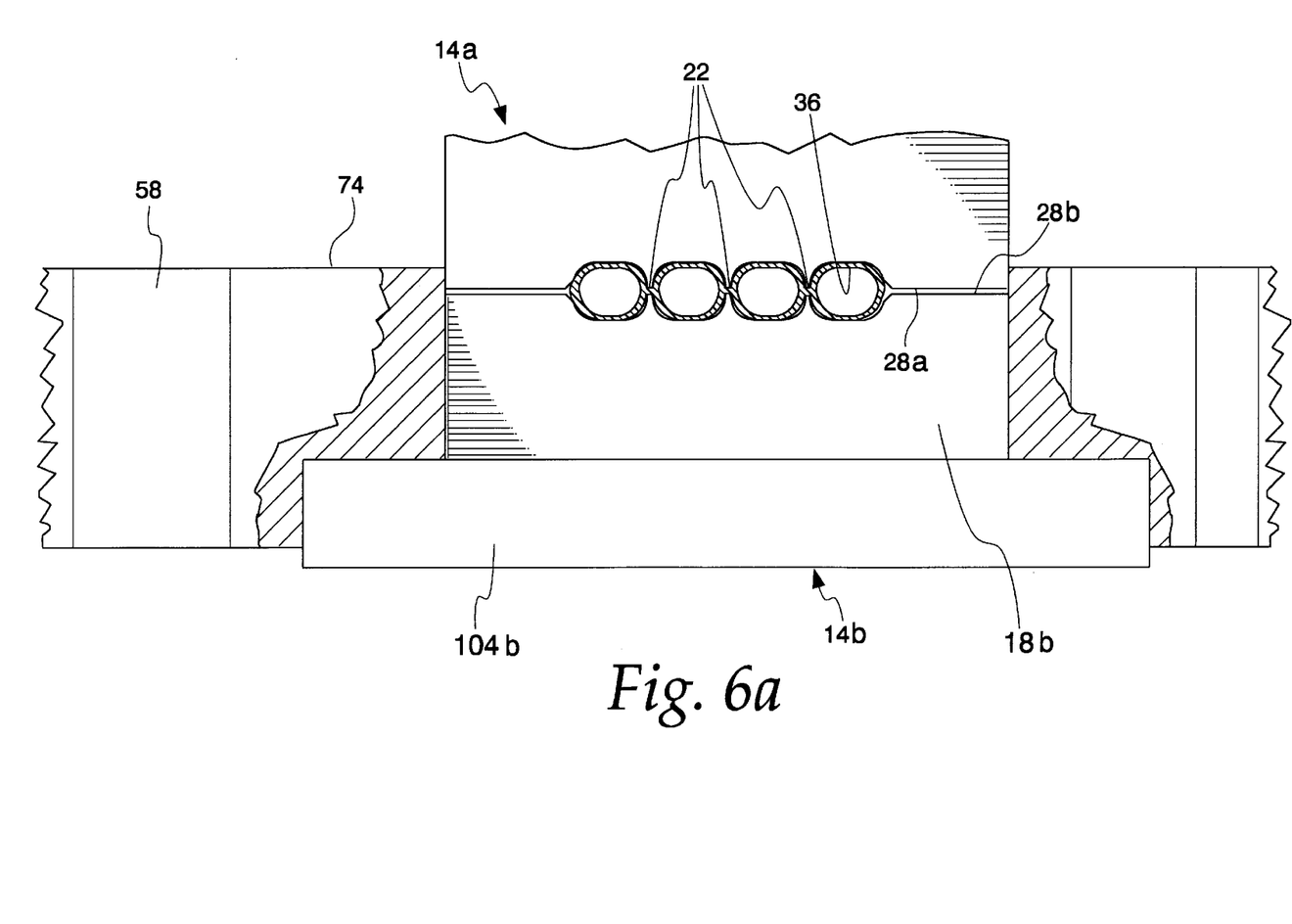
FIG. 6A is an enlarged elevational view of the apparatus of FIG. 1 with a portion of the platen broken away to show the dies in their operative position with sections of tubular members radially compressed in die bores between corresponding grooves of the dies and the connecting webs formed between the tube sections.

Referencing FIG. 1 to describe the apparatus 10 for forming the connecting webs 22 in greater detail, the die assemblies 14 are mounted to upper and lower plates 100 and 102, respectively, with the apparatus axis 106 oriented perpendicularly to the plates 100 and 102. The die assemblies 14 each include a mounting base 104 on which the die body 18 is mounted. The die assemblies 14 are provided in sets each including an upper die assembly 14a and a lower die assembly 14b with a pair of die sets on either side of a central axis 106 of the apparatus 10. The upper die assemblies 14a are mounted by way of mounting bores 108a formed in the base 104a of the assemblies 14a and aligned apertures 110a in the upper plate 100 to allow fasteners to secure the base 104a to the plate 100. Similarly, the lower plate 102 is provided with apertures 10b which, when aligned with mounting bores 108b of the lower die assemblies 14b, can received fasteners for securing the bases 104b of the lower die assemblies 14b to the lower plate 102. Thus, the apparatus 10 includes a pair of die sets including upper die assemblies 14a and lower die assemblies 14b with the die sets mounted to the upper and lower plates 100 and 102 so as to be positioned on either side of the central axis 106 of the apparatus 10 to form sets of webs 22 on either side of the axis 106. The platen 58 is supported between the plates 100 and 102 with the central axis 106 extending through the center of the platen 58. As previously mentioned, the lower die assemblies 14b are spaced on either side of the axis 106 so that their die bodies 18b project upwardly from the plate 102. The platen 58 is positioned so that the slots 96 and 98 are similarly arranged on either side of the apparatus axis 106 in alignment with the die bodies 18a and 18b so that when the die sets are brought together in their operative position, the lower die bodies 18b will project fully into the slots 96 and 98 and the upper die bodies 18a will project partially into slots 96 and 98, as shown in FIG. 6A.

With continued reference to FIG. 6A, there it can be seen that the platen 58 has one of the lower die bodies 18b projecting into one of its slots 96 and 98 so that the leading surface 28b is recessed slightly below the top surface 74 of the platen 58. Also, with the die bodies 18b of the lower die assemblies 14b in the slots 96 and 98, the grooves 30 and lands 32 of the dies 16 will span the width of their respective slot to substantially complete the grooves 60 and lands 62 of the platen 58.

Figure 6B:
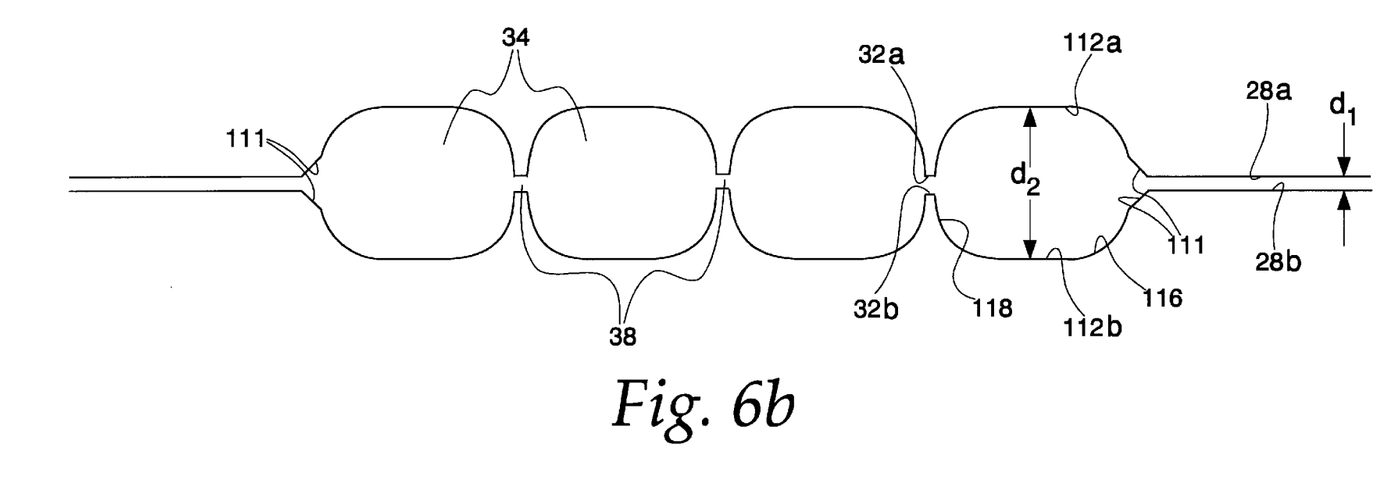
FIG. 6B is an enlarged diagrammatic view of the leading surfaces of the dies in their operative position as in FIG. 6 with the tube sections removed from the die bores.
Figures 7, 8:
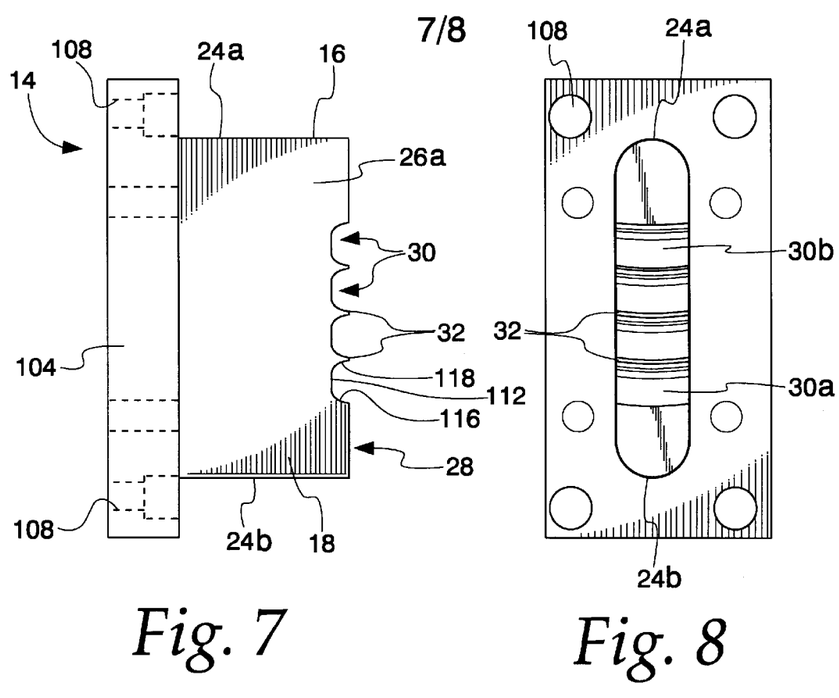
FIG. 7 is an enlarged side elevational view one of the dies showing the configuration of the grooves and lands according to the invention.
FIG. 8 is a plan view of the die of FIG. 7 with the curvature of the grooves and lands shown in magnified form.
Figure 9:
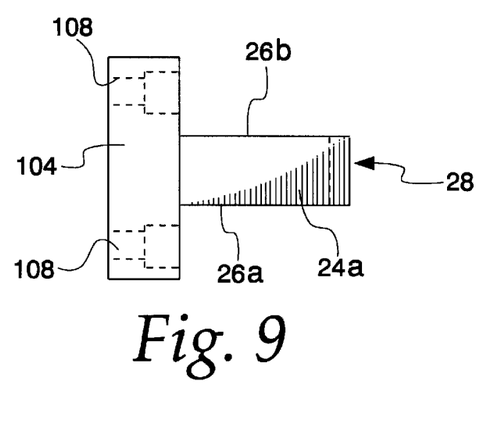
FIG. 9 is a front elevational view of the die of FIG. 7.

With the die assemblies 14a and 14b mounted to their respective plates 100 and 102 and the tubes 12a and 12b coiled in the platen grooves 60, the upper and lower plates 100 and 102 can be moved with respect to each other along axis 106, such as by a press, so that the aligned upper and lower dies 14a and 14b of the die sets are brought into engagement with the sections of the tubes 12a and 12b extending over the slots 96 and 98. The dies 16 are moved to their operative positions so that their leading surfaces 28 are spaced at a distance $D_1$ from one another, which is preferably between 0.010 and 0.014 inches apart, as best seen in FIG. 6B. At this position, facing lands 32 will likewise be positioned at the distance $D_1$ from each other which is sufficiently close to develop the RF energy potential therebetween for heating plastic in the web forming chambers 38. To avoid melting plastic tube walls of the innermost coil 48 and outermost coil 50 where there are no adjacent coils and thus they are not connected by webs 22 to adjacent coils, the junctures of the outermost grooves 30a and innermost grooves 30b with the leading surface 28 is provided with beveled surfaces 111 to increase the distance between the surfaces of the upper and lower die assemblies 14a and 14b thereat. This prevents the RF energy potential from developing sufficiently as to cause melting of the tubes 12a and 12b at the beveled surfaces 111 thus avoiding the formation of unsightly seams on the innermost and outermost coils 48 and 50, respectively.

It is preferred that the distance between the lands 32 and the bottom 112 of the grooves 30 be spaced so that when the upper and lower die assemblies 14a and 14b are brought to their operative position with the leading surfaces 28 and lands 32 spaced at the distance $D_1$, the die bores 34 formed by the grooves 30 will squeeze the tubular members 12a and 12b extruding portions of the tubing walls near the web forming chambers 38 therein so that they are trapped between opposing lands 32. Thus, with the preferred tube diameters of 0.258 inch, the distance from the groove bottom 112 which preferably is flat to the adjacent lands 32 is preferably approximately 0.097 inch so that a tube compression distance $D_2$ between aligned groove bottoms 112a and 112b is obtained which is equal to twice the distance between the groove bottoms 112 and the lands 32, plus the distance $D_1$, which, in the preferred form is 0.010 inch for a total distance $D_2$ of 0.024 inch, which is approximately 80% of the outer diameters of the tubular members 12a and 12b. In this manner, with the upper and lower die assemblies 14a and 14b, respectively, in their operative position as illustrated in FIG. 6A, the groove bottoms 112a and 112b will be at their compression distance $D_2$, i.e., 80% of the tube diameter, which is sufficient to compress and extrude the tube walls into the web forming chambers 38.

In the operative position, an RF energy generator 114 is fired applying RF energy to the dies 16 to develop an energy potential in the die forming chambers 38 and subject the tube wall portions therein to RF energy. In this manner, the portions of the tube walls in the web-forming chambers 38 are subject to rapid oscillations at the molecular level, causing the plastic material to break down and melt filling the web-forming chambers 38 and intimately intermingling with the melted material of the tube wall portion of an adjacent tube section that is also extruded in the chamber 38. Upon cooling and solidifying, the connecting webs 22 are formed with a uniform thickness corresponding to the distance $D_1$ between opposing lands 32a and 32b, as well as substantially corresponding in length to the length of the lands 32. By utilizing RF energy and dies 16 having carefully contoured leading surfaces 28 with grooves 30 and lands 32 formed therein for defining die bores 34 sized to squeeze and extrude tube wall portions into web forming chambers 38 between facing lands 32, much more consistent, accurate and precisely controlled connecting webs 22 are formed. This provides several advantages, including the fact that the pull force required for breaking the web can be closely regulated. This is of particular importance where the patients using the tubular assemblies 12 do not have the strength to exert a lot of energy in setting up their dialysis equipment such as may be required if the tubes have to be untaped and unravelled or pulled several times before they are disconnected from each other.

With the apparatus 10 utilizing the platen 58, a tube assembly 12 can be formed which will be radially coiled about the apparatus axis 106 producing a substantially circular or oblong tube assembly 12 having a flat configuration. In order for the connecting webs 22 to conform to the curvature of the tubes 12a and 12b when placed in the platen grooves 60, the grooves 30 and lands 32 of the dies 16 are radiused. The grooves 30 include arcuate portions that have a radius substantially equal to the radius of the corresponding coil of the coiled tubular members 12a and 12b such that the radius of the groove arcuate portions progressively decrease from the outer groove 30a to the inner groove 30b. More specifically and referring to FIGS. 7 and 8, each groove 30 includes opposite sides 116 and 118 which extend upwardly with a slightly curved slope on either side of the flat groove bottom surface 112 to the leading surface 28 or land 32. The groove sides 116 and 118 are radiused relative to the central axis 106 with the radii of the outer groove side 116 and inner groove side 118 for the outermost groove 30a being slightly larger than the radius for the corresponding sides of the adjacent groove with the radii of the groove sides progressively decreasing to the sides of the innermost groove 30b. Similarly, the lands 32 between the grooves 30 are radiused relative to the central axis 106 with the radius of the arcuate lands 32 progressively decreasing from the outermost land to the innermost land. More particularly, similar to the platen grooves 60 and lands 62, the die groove sides 116 and 118 and die lands 32 have radii which are different from the corresponding sides in an adjacent groove and adjacent lands, respectively, by the length of the diameter of the tubes 12 and the width of the lands 32. To properly form the webs 22 with a conforming curvature, the upper and lower dies 16 in a set are mirror images of one another with respect to the curvature of their grooves 30 and lands 32. Thus, the arcuate lands 32 of a die set cooperate to form a web-forming chamber 38 having a lengthwise arcuate shape for forming connecting webs 22 with an arcuate shape conforming to that of the arcuate chambers 38. In this manner, the webs 22 conform more closely to the curvature of the coils of the tubular members 12a and 12b.

Figure 10:
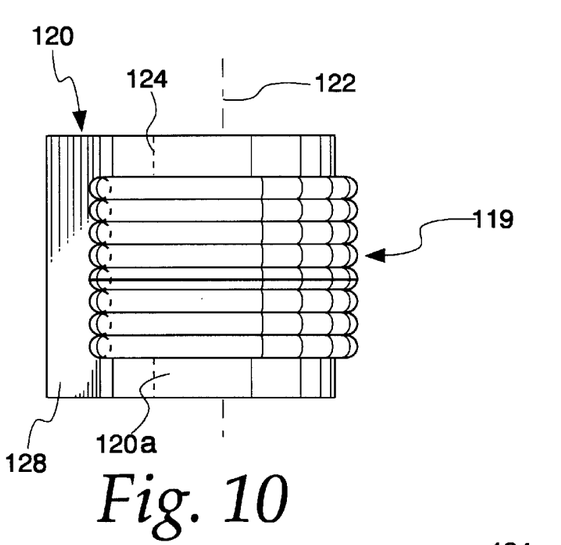
FIG. 10 is a front elevational view of another apparatus according to the invention having a mandrel for forming tubular assemblies in an axially coiled configuration.
Figure 11:
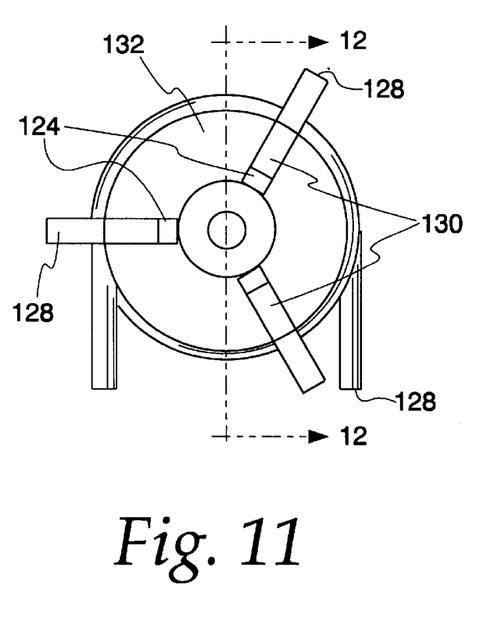
FIG. 11 is a plan view of the apparatus of FIG. 10 having a modified mandrel with circumferential grooves showing the dies in their operative position with the tubular members wound on the grooved cylindrical mandrel.
Figure 12:
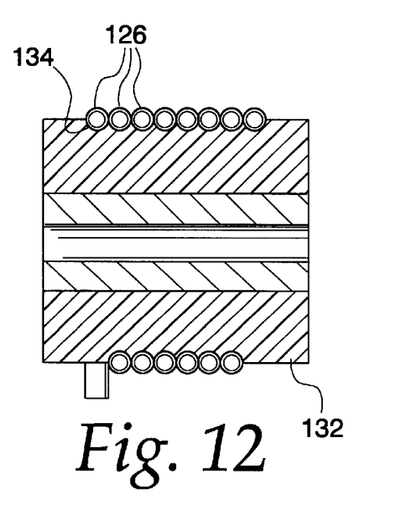
FIG. 12 is a cross-sectional view taken along lines 12—12 of FIG. 11.

Referring to FIGS. 10–12, the invention also contemplates forming tube assemblies 119 in an axially coiled configuration with connecting webs 22 formed by way of RF energy and RF energy conducting dies. More particularly, a tube mounting mandrel 120 is provided having a longitudinal axis 122. The dies utilized with the mandrel 120 are similar to the previously described dies 16 for conducting RF energy in having grooves 30 and lands 32 for forming connecting webs 22 between coils 126 of a plastic tubular member similar to the previously described tubular members 12a and 12b and which is coiled axially on the mandrel 120 about its axis 122. The mandrel 120 can include a longitudinal slot 124 formed in its outer surface 120a. The die set includes an outer die 128 and an inner die 130 with the inner die 130 mounted in the longitudinal slot 124. When multiple webs 22 are desired around the periphery of the coils 126, the outer cylindrical surface 120a of the mandrel 120 with the single longitudinal slot 124 is provided with a smooth finish such that the coils 126 can be rotated about the surface 120a a predetermined number of degrees for forming webs 122 at various locations around the coils 126.

As will be apparent, where the coils 126 cannot be readily rotated about the mandrel surface 120a, such as with a grooved mandrel 132 shown in FIGS. 11 and 12, a number of slots 124 can be provided for the inner dies 128. The number of slots 124 will determine the number of connecting webs 22 formed around the periphery of each coil with the illustrated embodiment showing a mandrel 132 having three longitudinal slots 124 with corresponding inner dies 130 mounted therein.

Where the mandrel 132 includes circumferential grooves 134 in which the coils 126 are seated, the mandrel 132 along with the inner dies 130 carried thereby can collapse to allow the tube assembly 119 with connecting webs 22 between coils 126 to slide off the mandrel 132. In the mandrel 120 having a smooth outer surface 120a, only the inner dies 130 need to be able to move within the slots 124 so that when the dies 128 and 130 are retracted away from the coils 126, the axially coiled tube assembly 119 can slide off of the mandrel 120.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention. For example, while the description of the radially coiled tube assembly 12 was in regards to two tubular members 12a and 12b, it is also contemplated that greater numbers of tubes can be radially coiled and connected with the dies 16 herein. Furthermore, the consistent and precise control over the formation of the webs 22 and thus the force required to break the webs 22 also allows the apparatus 10 to form webs that are readily peelable, for example, at one location along the lengths of several tubes, such as near the solution source, and to form other webs 22 which are more permanent in nature, for example, at another location along the lengths of the tubes, such as near the outlets into a cassette type pump.

I claim:

1. In an apparatus for forming tube assemblies of plastic tubular members which can be peeled to separate the tubular members from one another, a set of radio frequency dies placed about the tubular members to connect spaced portions of adjacent tubular members together, the die set comprising:

a pair of dies having respective leading surfaces which can be moved between a tube-receiving first position and an operative second position wherein in the first position the die surfaces are spaced at a first predetermined distance from each other and in the second position they are spaced at a second predetermined distance less than the first distance for forming the tube assembly, the dies being formed from an RF energy conducting material;

a plurality of cooperating grooves formed in the leading surfaces of the dies with grooves of the dies aligned with each other to cooperate to define die bores in the operative position, the die bores being sized to engage and radially compress the tubular members without occluding the flow passages of the tubes; and a land between pairs of adjacent grooves of the leading surfaces of the dies with corresponding lands on the die surfaces facing each other to define flow chambers for portions of the tubular members near the flow chambers which are plasticized upon application of RF energy to the dies for forming connecting webs of plastic between adjacent tubular members in the flow chambers when the dies are in their operative position.

2. The die set of claim 1 wherein the die bores are smaller than the diameter of the tubular members.

3. The die set of claim 1 wherein the dies are formed of a brass material.

4. The die set of claim 1 wherein the tubular members are coiled radially about an axis with the outer tubular member coil of the coiled tubular members having the largest radius from the axis and the inner tubular member coil having the smallest radius from the axis;

the plurality of cooperating grooves includes an outer groove and an inner groove; and the grooves include arcuate portions each having a radius substantially equal to the radius of the corresponding coil of the coiled tubular members with the radius of the arcuate portions progressively decreasing from the outer groove to the inner groove.

5. The die set of claim 4 wherein the arcuate portions of each groove includes an outer arcuate side and an inner arcuate side each having a radius with the radius of the inner side and the radius of the outer side of one of the grooves each being different from the radius of the respective inner and outer sides of another adjacent groove by the diameter of the tubular members and the width of the land between the grooves.

6. The die set of claim 1 wherein the lands have an arcuate shape having a radius with the radius of the arcuate lands progressively decreasing from an outer land to an inner land for forming arcuate shaped connecting webs between the coiled tubular members.

7. The die set of claim 1 wherein the dies have spaced ends and a groove edge closest to each end is beveled to prevent RF energy from plasticizing tube portions proximate the beveled edges.

* * * * *